United States Patent [19]

Tensmeyer

[11] 3,947,414

[45] Mar. 30, 1976

[54] CEFAMANDOLE DERIVATIVES

[75] Inventor: Lowell G. Tensmeyer, Indianapolis, Ind.

[73] Assignee: Eli Lilly and Company, Indianapolis, Ind.

[22] Filed: Dec. 23, 1974

[21] Appl. No.: 535,234

[52] U.S. Cl.............................. 260/243 C; 424/246
[51] Int. Cl.²................................... C07D 501/20
[58] Field of Search................................ 260/243 C

[56] References Cited
UNITED STATES PATENTS 3,840,531  10/1974  Greene............................ 260/243 C

*Primary Examiner*—Nicholas S. Rizzo
*Attorney, Agent, or Firm*—William C. Martens, Jr.; Everet F. Smith

[57] ABSTRACT

A novel crystalline derivative comprising the sodium salt of cefamandole, 1,4-dioxane, and water is herein defined. This derivative can be used to purify impure amorphous cefamandole sodium by the steps of preparing the crystalline derivative, isolating it from the mixture, and regenerating cefamandole sodium therefrom.

8 Claims, No Drawings

CEFAMANDOLE DERIVATIVES

BACKGROUND OF THE INVENTION

Cefamandole is a generic term used to identify a chemical compound, 7-(D-α-hydroxy-phenylacetamido)-3-(1-methyl-1H-tetrazol-5-ylthio)methyl-3-cephem-4-carboxylic acid, having the formula

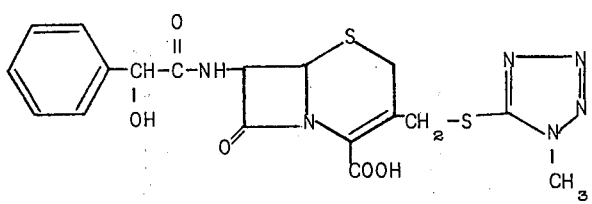

This compound is active as a broad spectrum antibiotic effective in controlling diseases caused by a wide variety of Gram-positive and Gram-negative microorganisms.

Cefamandole is one of the semi-synthetically produced cephalosporins. It can be prepared, for example, by treating 7-aminocephalosporanic acid, commonly known as 7-ACA, suitably protected in the 7-position, for example, by a formyl group, with 1-methyl-1H-tetrazole-5-thiol or an alkali metal, alkaline earth meatl, or ammonium salt thereof to produce the corresponding 7-formamido-3-(1-methyl-1H-tetrazol-5-ylthio)-methyl-3-cephem-4-carboxylic acid. This product then can be cleaved in accordance with known techniques to produce the corresponding 7-amino-3-(1-methyl-1H-tetrazol-5-ylthio) methyl-3-cephem-4-carboxylic acid, and the resulting cleaved product then can be acylated, for example, employing anhydro-O-carboxymandelic acid, to produce the desired cefamandole. The aforementioned sequence is typical of several methods which are available in the preparation of cefamandole. For example, the aforementioned acylation step can be carried out employing a mixed anhydride form of D-mandelic acid in which the hydroxyl group has been protected by a suitable blocking group, for example, a formyl or an acetyl group. The mixed anhydride then can be used as acylating agent for the 7-aminocephalosporin compound to form the hydroxy-protected cefamandole which then is cleaved to produce the desired cefamandole product. Alternative methods for effecting the acylation of 7-amino group are well known to those of ordinary skill in the art.

The source of the 7-formamido derivative of 7-ACA employed in the foregoing sequence is 7-ACA itself, and the latter can be obtained from cephalosporin C, more precisely known as 7-(5-aminoadipamido)cephalosporanic acid, which can be prepared by cultivating a cephalosporin C-producing organism in a suitable nutrient medium. The cephalosporin C can then be readily converted to the corresponding nucleus compound, 7-ACA, by cleaving the 5-aminoadipamyl side chain by known procedures.

A highly preferred form of cefamandole is its sodium salt derivative which has the following formula:

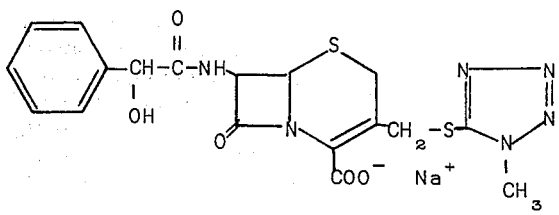

This form of cefamandole, however, does not exist in crystalline form, or at least a crystalline form has not as yet been discovered. As a result of this fact, two deficiencies have been noted. First, cefamandole sodium has been found to be purifiable to the extent necessary for administration only by very difficult and cumbersome techniques. Secondly, amorphous cefamandole sodium does not exhibit the degree of stability that one would desire, and certainly not such as one would expect from a corresponding crystalline structure.

In this context, therefore, it has become desirable to develop a crystalline form of cefamandole sodium, which form would be useful in purifying cefamandole sodium itself. This purification sequence then would comprise preparation of a crystalline derivative of cefamandole sodium from an impure or relatively impure lot of cefamandole sodium. The crystalline derivative then could be isolated from the impure mixture leaving impurities behind. Any such desirable crystalline derivative then would be usable as such or would exhibit properties which would permit its ready decomposition with regeneration of cefamandole sodium itself in purified form.

Such a derivative would permit purification of impure amorphous cefamandole sodium; additionally, it would permit the retention of cefamandole sodium in a highly stable form, which form could be decomposed with regeneration of the cefamandole sodium at some point prior to packaging of the cefamandole sodium in a unit suitable for ultimate administration.

Such a discovery forms the basis of this invention. It is an object, therefore, of this invention to provide a novel composition of matter comprising a stable, crystalline derivative of cefamandole sodium.

It is a further object of this invention to provide a method for purifying cefamandole sodium by preparing and recovering a defined crystalline derivative thereof and subsequently decomposing the derivative to recover cefamandole sodium itself.

SUMMARY OF THE INVENTION

Thus, one aspect of this invention is a crystalline composition of matter comprising a complex of the sodium salt of cefamandole, 1,4-dioxane, and water.

In another aspect of this invention there is provided a process for purifying the sodium salt of cefamandole which comprises converting said salt containing impurities to a crystalline complex comprising cefamandole sodium, 1,4-dioxane, and water, separating said crystalline complex from said impurities, and decomposing said crystalline complex to recover purified cefamandole sodium.

DETAILED DESCRIPTION OF THE INVENTION

As indicated hereinabove, this invention relates to a novel composition of matter as well as to a process for purifying the sodium salt of cefamandole.

The novel composition of matter of this invention comprises cefamandole sodium, 1,4-dioxane, and water. Relative to the cefamandole sodium, the ratio on a molar basis of the 1,4-dioxane present in the composition of this invention is from 0.5 to 1.0. Additionally, the water which is present in the crystalline complex can range on a molar basis up to about 1.0, and generally from about 0.5 to about 1.0, based on the cefamandole sodium.

Crystal structure studies have established that a single 1,4-dioxane molecule accomodates two cefamandole molecules by a hydrogen bonding arrangement. A hydrogen bond exists between each of the oxygens of the 1,4-dioxane molecule and the amide hydrogen in the 7-position of each of two cefamandole molecules. Effectively, therefore, a single 1,4-dioxane molecule binds two cefamandole molecules, one at each of the two oxygens of its structure. This accounts for one 1,4-dioxane molecule for each two cefamandole sodium molecules. The relative locations of the three molecules which comprise this unit give rise to a spatial arrangement which includes a gap between this unit and similar units of three molecules nearby. This gap is of such size and location as to readily accommodate an additional 1,4-dioxane molecule as well as sufficient water to account for up to about 1 mole of water per mole of cefamandole. However, the latter 1,4-dioxane and any water are held primarily by the physical dimensions of the crystalline structure. Any bonding forces attributable to the latter 1,4-dioxane molecule and the water are, at most, minimal. For this reason, it is possible for the crystalline complex of this invention to contain either one or two molecules of 1,4-dioxane per each two molecules of cefamandole and to have moisture present in the range representative of up to one molecule of water per each molecule of cefamandole.

Employing the method described herein for preparing the composition of matter of this invention will result in formation of the crystalline product which contains an equimolar quantity of cefamandole sodium and 1,4-dioxane, and water in an amount approximately equimolar to the cefamandole sodium. This latter composition constitutes a preferred embodiment of this invention.

A composition containing reduced amounts of 1,4-dioxane and of water can be prepared by treating the firstmentioned composition under conditions conducive to remove onehalf of the 1,4-dioxane and the water, neither of which participates in the bonding influences which go to establish the core crystalline structure. These conditions include, for example, heating the composition, preferably at a temperature of from about 25°C. to about 50°C., or subjecting the composition to vacuum conditions, or both.

The 1,4-dioxane and water removal is sufficient to remove an equivalent of one molecule of 1,4-dioxane per each two molecules of cefamandole sodium and to remove substantially all water from the composition. It has been discovered that in the removal conditions of temperature and/or vacuum, water is substantially entirely removed from the composition prior to any removal of the unbonded 1,4-dioxane. However, because of the rapidity of removal it is difficult to selectively remove only the water with retention of the unbonded 1,4-dioxane in the resultant composition.

Another preferred composition of this invention, therefore, is one which comprises, on a molar basis, a 2:1 ratio of cefamandole sodium and 1,4-dioxane.

The novel crystalline form provided by this invention has the following unique X-ray powder diffraction characteristics at $\lambda = 1.5405$ using a Cu:Ni 45 kv. 20 ma. source.

| Spacing d | Relative intersities $I/I_1$ |
| --- | --- |
| 17.90 | .30 |
| 12.10 | .60 |
| 10.00 | .30 |
| 8.52 | .60 |
| 7.16 | .10 |
| 6.30 | 1.00 |
| 6.16 | .30 |
| 5.57 | .30 |
| 5.25 | .60 |
| 4.99 | .40 |
| 4.33 | .30 |
| 4.19 | 1.00 |
| 3.95 | .70 |
| 3.80 | .30 |
| 3.59 | .60 |
| 3.32 | .20 |
| 3.16 | .10 |
| 3.04 | .15 |
| 2.90 | .10 |
| 2.82 | .10 |
| 2.68 | .20 |
| 2.59 | .05 |
| 2.43 | .05 |
| 2.31 | .05 |
| 2.18 | .15 |
| 2.11 | .05 |
| 2.04 | .05 |
| 1.98 | .15 |
| 1.88 | .10 |
| 1.73 | .05 |

The above X-ray powder diffraction pattern is representative of any of the aforedescribed compositions since it is a measure of the fixed bonding arrangements. Any additional 1,4-dioxane and water is only loosely held and does not therefore alter the resultant X-ray powder diffraction pattern to any significant degree.

This is also true of the lattice parameters obtained by X-ray of a single crystal. These parameters are as follows:

| Space group | $P2_1$ |
| --- | --- |
| a = 12.67A | |
| b = 37.84A | $\beta = 89.79°$ |
| c = 11.75A | |

The novel crystalline form provided by this invention is almost cubic in appearance. More often one dimension is much less than the other two, giving rise to a square disc appearance. It is apparent, however, that the crystalline habit is not an essential characteristic of the crystalline complex of this invention.

The process aspect of this invention provides a method for purification of the sodium salt of cefamandole by the sequence of preparing the novel crystalline complex of this invention, separating the crystalline complex from the preparation medium, and decomposing the crystalline complex to regenerate the sodium salt of cefamandole in purified form.

Depending upon the conditions employed in the initial preparation of the crystalline complex of this invention, the preparation can be quite rapid, being completed in a matter of a few hours, or it can take an extended period of time, sometimes from about 4 to about 8 weeks. However, once an initial preparation of the complex has been accomplished, the time required for subsequent preparations can be substantially reduced merely by the availability of crystals from the first preparation, which crystals can be employed to seed the medium in subsequent preparations. The important factor in determining the length of preparation time is the concentration of the solution in which the complex is generated and from which it is isolated. The solution must be at least saturated; however, the preparation time, even without seeding, can be greatly diminished when the conditions of preparation are such that the complex is derived from a highly supersaturated solution.

Preparation of the crystalline complex of this invention is accomplished by dissolving the sodium salt of cefamandole in a mixture of 1,4-dioxane and water containing from about 40 mole percent to about 70 mole percent 1,4-dioxane relative to the solvent mixture. Sufficient cefamandole sodium is dissolved in the mixture to obtain at least a saturated solution thereof. The mixture is maintained at a temperature of from about 0°C. to about 20°C., preferably from about 3°C. to about 16°C., for a time sufficient to produce crystallization of the crystalline complex of this invention. As indicated hereinabove, this time period may extend to several weeks. As also indicated hereinabove, the time for crystallization can be greatly reduced by incorporating into the saturated solution seeds of the crystalline complex obtained from a previous preparation or by carrying out the preparation under supersaturated conditions.

After the solution has been maintained at the requisite temperature for a period sufficient to accomplish the extent of crystal growth which is desired, the crystals can be harvested from the mixture by filtration. Residual amounts of the mother liquor, containing undesirable impurities, can be removed from the harvested crystals by washing the crystals with 1,4-dioxane or a mixture of water and 1,4-dioxane. Preferably, any such washing is carried out using a cold (about 4°C. to about 8°C.) mixture of water and 1,4-dioxane in which the 1,4-dioxane is present in an amount relative to the water at least as great as that employed in the preparation of the complex. It is highly preferred to initially wash the complex with a 90:10 mixture of 1,4-dioxane and water and subsequently to wash the complex with 1,4-dioxane itself.

The resulting crystals then can be stored at room temperature or below for extended periods with little or no decomposition. Alternatively, the crystals can be decomposed to regenerate the cefamandole sodium in purified form.

Decomposition of the crystalline complex with regeneration of cefamandole sodium can be accomplished by dissolving the crystals in a quantity of water sufficient to prepare a clear solution and then evaporating the solvent from the mixture to obtain the purified sodium salt of cefamandole. Preferably, the desired purified amorphous sodium salt of cefamandole is regenerated by lyophilizing the aqueous solution in a dry ice-acetone bath. The dioxane and water which are present in the crystalline complex are readily removed under evaporative conditions since the dioxane which is present azeotropes with the water during its removal such that the resulting product is both anhydrous and dioxane-free.

The resulting amorphous sodium salt of cefamandole is pure and ready for use as an active anti-bacterial agent.

The following examples are provided to illustrate the teaching of this invention. They are not intended to be limiting upon the general scope thereof.

EXAMPLE 1 — Slow Preparation of a Crystalline Complex of Cefamandole Sodium, 1,4-Dioxane, and Water On Day 1, 500 mg. of the sodium salt of cefamandole were weighed into a 2 ml. vial. The vial was filled at 15°C. with a mixture of 55 mole percent of 1,4-dioxane in water. The color of the resulting mixture was quite dark, the cefamandole sodium being relatively impure. The mixture, maintained at 15.90°C., was examined on Day 3; solution was as yet not complete. On Day 6, with the temperature maintained at about 15.7°C., the appearance of the mixture was about the same as before. On Day 14, the mixture was fairly clear but quite dark in color.

On Day 22, the mixture contained one or two large crystals floating in the solution; however, there was yet much very small undissolved material in the mixture. The temperature of the mixture was 15.32°C. The temperature was lowered to 11.5°C., and on Day 24 there was little if any change in appearance, the one or two crystals remaining visible in the mixture. On Day 27, the temperature of the mixture was 10.40°C., and some crystalline material was present. However, it could not be determined whether this crystalline material represented an increased amount. On Day 28, the mixture, maintained at 8.80°C., appeared to exhibit some growth of crystals. The crystals were again apparent on Day 29, the temperature of the mixture being 7.25°C.

On Day 37, wiht the temperature at 4.32°C., the vial contained myriads of what looked like crystals. On Day 38, the mixture, at 3.75°C., still contained crystals. The solvent had not frozen, indicating that the crystals which had formed should not be crystals of solvent.

On Day 41, crystals in the mixture were sampled by pipette, placed on a slide, and the liquid blotted from the crystals by filter paper. The crystals were found to be very sticky due to the presence of the mother liquor. Their initial appearance, however, appeared quite good, albeit fairly small single crystals.

Another sample of the crystals was removed from the mixture. This samples was washed with cold dioxane, and the resulting crystalline residue was found to be much easier to handle. Infrared analysis was run on the washed crystals. The analysis indicated the presence both of dioxane and cefamandole sodium.

A thin-layer chromatogram was run and compared with that of cefamandole sodium itself. The two substances had identical $R_f$ values.

EXAMPLE 2 — Preparation of the Crystalline Complex by Seeding

A solution of 20 grams of the sodium salt of cefamandole in 40 ml. of a mixture containing 60 mole percent 1,4dioxane and 40 mole percent of water was prepared. When dissolution was complete at about 15°C., the solution was filtered, and the filtrate was seeded with a large single crystal of the previously prepared crystalline complex of cefamandole sodium, 1,4-dioxane, and water. The temperature of the mixture then was rapidly lowered to 5°C. and maintained thereat overnight. On the next day, the solution contained many crystals so as to be almost a slurry. The mixture was refrigerated at about −1°C. for several hours, the mixture then was filtered, and the filtered product was washed with a mixture containing 80 mole percent dioxane and 20 mole percent water.

The filtered, washed crystals were air-dried for about one hour and then were transferred to a flask and dried under moderately reduced pressure to obtain a yield of 10 g. of a dried crystalline complex of cefamandole sodium, 1,4-dioxane, and water.

EXAMPLE 3 — Rapid Preparation of a Crystalline Complex of Cefamandole Sodium, 1,4-Dioxane, and Water To a round bottom flask maintained at 15°C. were added 150 g. of cefamandole sodium, 263 ml. of 1,4-dioxane, and 37 ml. of water. The resulting mixture was stirred overnight to effect dissolution.

On the following day crystals of the complex spontaneously appeared. The temperature of the mixture was lowered to 10°C. and maintained thereat overnight. On the following morning the temperature was lowered to and maintained at 5°C. until afternoon at which time the temperature was further lowered to about 1°C. The mixture was maintained at the lowered temperature overnight. The mixture then was filtered, and the collected crystalline solid was washed with a mixture comprising a 90:10 molar ratio of 1,4-dioxane and water. The crystals then were spread on a large filter paper and allowed to air dry; the crystals then were transferred to a round bottom flask and dried at moderately reduced pressure to obtain the crystalline complex of cefamandole sodium, 1,4-dioxane, and water.

EXAMPLE 4 — Regeneration of Cefamandole Sodium

To about 15 ml. of water were added 5.0 g. of the crystals obtained in Example 2. The resulting solution was clear and water-white. The mixture was frozen by rotation in a round bottom flask in dry ice-acetone and was lyophilized overnight to obtain a highly pure, amorphous cefamandole sodium.

I claim:

1. A crystalline complex comprising the sodium salt of cefamandole, 1,4-dioxane, and water.

2. Composition of claim 1, in which 1,4-dioxane and the sodium salt of cefamandole are present in approximately an equimolar ratio and water is present in a molar ratio of from about 0.5 to about 1.0 based upon the cefamandole sodium.

3. A crystalline complex comprising a 2:1 molar ratio of the sodium salt of cefamandole and 1,4-dioxane.

4. Process for purifying the sodium salt of cefamandole, which comprises converting said salt containing impurities to the crystalline complex of cefamandole sodium, 1,4-dioxane, and water, separating said crystalline complex from said impurities, and decomposing said crystalline complex to recover purified cefamandole sodium.

5. Process of claim 4, in which the crystalline complex is prepared from at least a saturated solution of the sodium salt of cefamandole in a mixture of 1,4-dioxane and water containing from about 40 mole percent to about 70 mole percent 1,4-dioxane relative to the solvent mixture.

6. Process of claim 5, in which the solution is maintained at a temperature of from about 0°C. to about 20°C. for a time sufficient to produce crystallization of the crystalline complex.

7. Process of claim 6, in which the crystalline complex is decomposed to the sodium salt of cefamandole by dissolving the separated crystals in water and evaporating the solvent from the solution.

8. Process of claim 7, in which the sodium salt is recovered from the aqueous solution by lyophilization.

* * * * *